United States Patent
Schneider et al.

(10) Patent No.: US 10,246,640 B2
(45) Date of Patent: Apr. 2, 2019

(54) MIXTURES OF AT LEAST ONE DIALKYLPHOSPHINIC ACID WITH AT LEAST ONE OTHER DIALKYLPHOSPHINIC ACID THAT IS DIFFERENT THEREFROM, METHOD FOR PRODUCTION THEREOF, AND USE THEREOF

(71) Applicant: Clariant International Ltd., Muttenz (CH)

(72) Inventors: Fabian Schneider, Eppelheim (DE); Frank Osterod, Köln (DE); Harald Bauer, Kerpen (DE); Martin Sicken, Köln (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 15/713,547

(22) Filed: Sep. 22, 2017

(65) Prior Publication Data

US 2018/0010047 A1    Jan. 11, 2018

Related U.S. Application Data

(62) Division of application No. 14/364,972, filed as application No. PCT/EP2012/005175 on Dec. 13, 2012, now abandoned.

(30) Foreign Application Priority Data

Dec. 21, 2011   (DE) .................. 10 2011 121 900

(51) Int. Cl.
  *C07F 9/30* (2006.01)
  *C08G 59/14* (2006.01)
  *C09K 21/12* (2006.01)

(52) U.S. Cl.
  CPC ............... *C09K 21/12* (2013.01); *C07F 9/30* (2013.01); *C07F 9/301* (2013.01); *C08G 59/1488* (2013.01)

(58) Field of Classification Search
  None
  See application file for complete search history.

(56) References Cited

U.S. PATENT DOCUMENTS

| | | | | |
|---|---|---|---|---|
| 4,342,846 A | * | 8/1982 | Silberberg ............ | C08L 51/003 525/166 |
| 5,780,534 A | * | 7/1998 | Kleiner .................. | C07F 9/30 524/133 |
| 6,300,516 B1 | * | 10/2001 | Weferling ............... | C07F 9/30 562/8 |
| 6,355,832 B1 | | 3/2002 | Weferling et al. | |
| 6,420,459 B1 | * | 7/2002 | Horold .................... | C08K 3/22 523/451 |
| 7,635,785 B2 | | 12/2009 | Bauer et al. | |
| 8,293,938 B2 | | 10/2012 | Hill et al. | |
| 8,764,880 B2 | | 7/2014 | Zhou et al. | |
| 9,481,831 B2 | | 11/2016 | Bauer et al. | |

(Continued)

FOREIGN PATENT DOCUMENTS

| | | |
|---|---|---|
| DE | 197 52 735 | 7/1999 |
| EP | 1 544 205 | 6/2005 |
| WO | WO 99/28327 | 6/1999 |
| WO | WO-2006090751 A1 * | 8/2006 ........... C08K 5/5313 |
| WO | WO 2009/010188 | 1/2009 |

OTHER PUBLICATIONS

Kuwata, WO2006090751 English Machine Language Translation, Aug. 15, 2016 (Year: 2016).*

(Continued)

*Primary Examiner* — Christopher M Rodd

(74) *Attorney, Agent, or Firm* — Morgan, Lewis & Bockius LLP

(57) ABSTRACT

Mixtures of at least one dialkylphosphinic acid with at least one other dialkylphosphinic acid that is different therefrom, method for production thereof, and use thereof.

The invention relates to a mixture of at least one dialkylphosphinic acid of the formula (I)

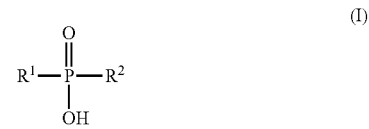

(I)

in which $R^1$, $R^2$ are the same or different and are each $C_1$-$C_{18}$-alkyl, $C_2$-$C_{18}$-alkenyl, $C_6$-$C_{18}$-aryl, $C_7$-$C_{18}$-alkylaryl, with at least one different dialkylphosphinic acid of the formula (II)

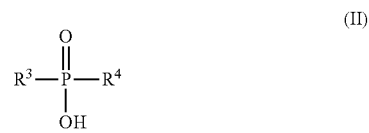

(II)

in which $R^3$, $R^4$ are the same or different and are each $C_1$-$C_{18}$-alkyl, $C_2$-$C_{18}$-alkenyl, $C_6$-$C_{18}$-aryl and/or $C_7$-$C_{18}$-alkylaryl, with the proviso that at least one of the $R^3$ and $R^4$ radicals is different than $R^1$ and $R^2$.

2 Claims, No Drawings

(56) References Cited

U.S. PATENT DOCUMENTS

| | | |
|---|---|---|
| 9,505,904 B2 | 11/2016 | Bauer et al. |
| 2011/0263754 A1* | 10/2011 | Wilson ................. C08K 5/0091 523/459 |
| 2014/0309339 A1 | 10/2014 | Schneider et al. |
| 2014/0309340 A1 | 10/2014 | Schneider et al. |
| 2014/0329933 A1 | 11/2014 | Schneider et al. |
| 2014/0371361 A1 | 12/2014 | Bauer et al. |
| 2015/0005421 A1 | 1/2015 | Schneider et al. |
| 2015/0005427 A1 | 1/2015 | Bauer et al. |
| 2015/0018464 A1 | 1/2015 | Bauer et al. |

OTHER PUBLICATIONS

PCT international Search Report for PCT/EP2012/005175, dated Mar. 8, 2013.
PCT International Preliminary Report on Patentability for PCT/EP2012/005175, dated Jun. 24, 2014.
English abstract for DE 197 52 735 dated Jul. 1, 1999.
Laetitia Coudray et al., "Allylic Phosphinates via Palladium-Catalyzed Allylation of H-Phosphinic Acids with Allylic Alcohols." XP-002561368, Organic Letters 2008, vol. 10, No. 6, pp. 1123-1126.
E. Andrew Boyd et al., "Facile Synthesis of Phosphorus-containing Heterocycles". *Tetrahedron Letters*, vol. 37, No. 30, pp. 5425-5426.

* cited by examiner

MIXTURES OF AT LEAST ONE DIALKYLPHOSPHINIC ACID WITH AT LEAST ONE OTHER DIALKYLPHOSPHINIC ACID THAT IS DIFFERENT THEREFROM, METHOD FOR PRODUCTION THEREOF, AND USE THEREOF

CROSS REFERENCE TO RELATED APPLICATION

This application is a divisional application of U.S. Ser. No. 14/364,972, by Schneider et al., the entire disclosure of which is hereby incorporated herein by reference.

The present invention relates to mixtures of at least one dialkylphosphinic acid with at least one other, different dialkylphosphinic acid, to a process for preparation thereof and use thereof.

In the production of printed circuit boards, which are being used to an increasing degree in various devices, for example computers, cameras, cellphones, LCD and TFT screens and other electronic devices, different materials, especially polymers, are being used. These include particularly thermosets, glass fiber-reinforced thermosets and thermoplastics. Owing to their good properties, epoxy resins are used particularly frequently.

According to the relevant standards (IPC-4101, Specification for Base Materials for Rigid and Multilayer Printed Boards), these printed circuit boards must be rendered flame-retardant.

The thermal expansion of printed circuit boards in the course of production thereof is a problem. The conditions of electronics manufacture for printed circuit boards require that printed circuit boards withstand high thermal stresses without damage or deformation. The application of conductor tracks (lead-free soldering) to printed circuit boards is effected at temperatures up to about 260° C. It is therefore important that printed circuit boards do not warp under thermal stress and the products remain dimensionally stable.

Thermal expansion is significant particularly even in the case of prepregs (short form of "preimpregnated fibers") and laminates, since these constitute the initial forms or precursors of printed circuit boards.

It is thus important to minimize the thermal expansion of test specimens in order to obtain a good, dimensionally stable product (finished printed circuit board).

It is an object of the present invention to modify polymers for prepregs, printed circuit boards and laminates such that they are subject only to very low thermal expansion—if any at all—and dimensional stability is fulfilled.

This object is achieved by mixtures of at least one dialkylphosphinic acid of the formula (I)

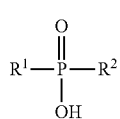

(I)

in which
$R^1$, $R^2$ are the same or different and are each $C_1$-$C_{18}$-alkyl, $C_2$-$C_{18}$-alkenyl, $C_6$-$C_{18}$-aryl, $C_7$-$C_{18}$-alkylaryl,
with at least one different dialkylphosphinic acid of the formula (II)

(II)

in which
$R^3$, $R^4$ are the same or different and are each $C_1$-$C_{18}$-alkyl, $C_2$-$C_{18}$-alkenyl, $C_6$-$C_{18}$-aryl and/or $C_7$-$C_{18}$-alkylaryl,
with the proviso that at least one of the $R^3$ and $R^4$ radicals is different than $R^1$ and $R^2$.

Preferably, $R^1$ and $R^2$ are the same or different and are each methyl, ethyl, n-propyl, isopropyl, n-butyl, isobutyl, tert-butyl, n-pentyl, isopentyl, n-hexyl, isohexyl and/or phenyl.

Preferably, $R^3$ and $R^4$ are the same or different and are each methyl, ethyl, n-propyl, isopropyl, n-butyl, isobutyl, tert-butyl, n-pentyl, isopentyl, n-hexyl, isohexyl and/or phenyl, with the proviso that at least one of the $R^3$ and $R^4$ radicals is different than $R^1$ and $R^2$.

The mixtures preferably comprise 0.1 to 99.9% by weight of dialkylphosphinic acid of the formula (I) and 99.9 to 0.1% by weight of a different dialkylphosphinic acid of the formula (II).

More preferred are mixtures comprising 40 to 99.9% by weight of dialkylphosphinic acid of the formula (I) and 60 to 0.1% by weight of a different dialkylphosphinic acid of the formula (II).

Further preferred are mixtures comprising 60 to 99.9% by weight of dialkylphosphinic acid of the formula (I) and 40 to 0.1% by weight of a different dialkylphosphinic acid of the formula (II).

Also preferred are mixtures comprising 80 to 99.9% by weight of dialkylphosphinic acid of the formula (I) and 20 to 0.1% by weight of a different dialkylphosphinic acid of the formula (II).

Likewise preferred are mixtures comprising 90 to 99.9% by weight of dialkylphosphinic acid of the formula (I) and 10 to 0.1% by weight of a different dialkylphosphinic acid of the formula (II).

Additionally preferred are mixtures comprising 95 to 99.9% by weight of dialkylphosphinic acid of the formula (I) and 5 to 0.1% by weight of a different dialkylphosphinic acid of the formula (II).

Particular preference is given, however, to mixtures comprising 98 to 99.9% by weight of dialkylphosphinic acid of the formula (I) and 2 to 0.1% by weight of a different dialkylphosphinic acid of the formula (II).

The dialkylphosphinic acids are preferably diethylphosphinic acid, ethylpropylphosphinic acid, ethylbutylphosphinic acid, ethylpentylphosphinic acid, ethylhexylphosphinic acid, dipropylphosphinic acid, propylbutylphosphinic acid, propylpentylphosphinic acid, propylhexylphosphinic acid, dibutylphosphinic acid, butylpentylphosphinic acid, butylhexylphosphinic acid, dipentylphosphinic acid, pentylhexylphosphinic acid and/or dihexylphosphinic acid.

Particular preference is given in accordance with the invention to mixtures comprising 98 to 99.9% by weight of diethylphosphinic acid and 2 to 0.1% by weight of butylethylphosphinic acid.

The inventive mixtures preferably further comprise at least one synergist, the synergist being a nitrogen-containing compound such as melem, melam, melon, melamine borate, melamine cyanurate, melamine phosphate, dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate, melamine polyphosphate, melam polyphosphate, melem polyphosphate and/or melon polyphosphate;
aluminum compounds such as aluminum hydroxide, halloysite, sapphire products, boehmite, nanoboehmite;
magnesium compounds such as magnesium hydroxide;
tin compounds such as tin oxides;
antimony compounds such as antimony oxides;
zinc compounds such as zinc oxide, zinc hydroxide, zinc oxide hydrate, zinc carbonate, zinc stannate, zinc hydroxystannate, zinc silicate, zinc phosphate, zinc borophosphate, zinc borate and/or zinc molybdate;
silicon compounds such as silicates and/or silicones;
phosphorus compounds such as phosphinic acids and salts thereof, phosphonic acids and salts thereof and/or phosphine oxides, phosphazenes and/or piperazine (pyro)phosphates;
carbodiimides, piperazines, (poly)isocyanates, styreneacrylic polymers; and/or carbonylbiscaprolactam;
nitrogen compounds from the group of oligomeric esters of tris(hydroxyethyl) isocyanurate with aromatic polycarboxylic acids, or benzoguanamine, acetoguanamine, tris(hydroxyethyl) isocyanurate, allantoin, glycoluril, cyanurates, cyanurate-epoxide compounds, urea cyanurate, dicyanamide, guanidine, guanidine phosphate and/or sulfate.

The mixtures preferably comprise 99 to 1% by weight of mixtures of at least one dialkylphosphinic acid of the formula (I) and one different dialkylphosphinic acid of the formula (II) and 1 to 99% by weight of synergist.

The invention also relates to a process for preparing mixtures, which comprises reacting a phosphorus source with an initiator and an olefin and treating the alkylated phosphorus compound thus obtained with a mineral acid and converting it, by concentration and workup, to a mixture of at least one dialkylphosphinic acid of the formula (I) and at least one different dialkylphosphinic acid of the formula (II).

Preferably, the phosphorus source is a phosphinic salt, the olefin is ethylene and the mineral acid is sulfuric acid or hydrochloric acid, and the free-radical initiator is 2,2'-azobis (2-amidinopropane) dihydrochloride, 2,2'-azobis(N,N'-dimethyleneisobutyramidine) dihydrochloride, azobis(isobutyronitrile), 4,4'-azobis(4-cyanopentanoic acid) and/or 2,2'-azobis(2-methylbutyronitrile) or hydrogen peroxide, ammonium peroxodisulfate, potassium peroxodisulfate, dibenzoyl peroxide, di-tert-butyl peroxide, peracetic acid, diisobutyryl peroxide, cumene peroxyneodecanoate, tert-butyl peroxyneodecanoate, tert-butyl peroxypivalate, tert-amyl peroxypivalate, dipropyl peroxydicarbonate, dibutyl peroxydicarbonate, dimyristyl peroxydicarbonate, dilauroyl peroxide, 1,1,3,3-tetramethylbutyl peroxy-2-ethylhexanoate, tert-amyl peroxy-2-ethylhexylcarbonate, tert-butyl peroxyisobutyrate, 1,1-di(tert-butylperoxy)cyclohexane, tert-butyl peroxybenzoate, tert-butyl peroxyacetate, tert-butyl peroxydiethylacetate, tert-butyl peroxyisopropylcarbonate, 2,2-di(tert-butylperoxy)butane, tert-amyl hydroperoxide and/or 2,5-dimethyl-2,5-di(tert-butylperoxy)hexane.

The process is preferably executed in such a way that sodium phosphinate is reacted with ethylene and then with dilute sulfuric acid, concentrated, filtered and distilled, in order to obtain a mixture of diethylphosphinic acid and butylethylphosphinic acid.

Preferably, the reaction takes place in a solvent and the solvent is an alcohol, acid or water.

The reaction temperature is preferably between 50 and 150° C.

The invention also encompasses the use of mixtures of at least one dialkylphosphinic acid of the formula (I) and at least one different dialkylphosphinic acid of the formula (II) as an intermediate for further syntheses, as a binder, as a crosslinker or accelerator in the curing of epoxy resins, polyurethanes and unsaturated polyester resins, as polymer stabilizers, as crop protection compositions, as sequestrants, as a mineral oil additive, as an anticorrosive, in washing and cleaning composition applications and in electronics applications.

More particularly, the invention encompasses the use of mixtures of at least one dialkylphosphinic acid of the formula (I) and at least one different dialkylphosphinic acid of the formula (II) as a flame retardant, especially as a flame retardant for clearcoats and intumescent coatings, as a flame retardant for wood and other cellulosic products, as a reactive and/or nonreactive flame retardant for polymers, for production of flame-retardant polymer molding compositions, for production of flame-retardant polymer moldings and/or for rendering polyester and pure and blended cellulose fabrics flame-retardant by impregnation, and as a synergist.

The invention also relates to a flame-retardant thermoplastic or thermoset polymer molding composition and to polymer moldings, films, filaments and fibers comprising 0.5 to 45% by weight of mixtures of at least one dialkylphosphinic acid of the formula (I) and at least one different dialkylphosphinic acid of the formula (II), 0.5 to 99.5% by weight of thermoplastic or thermoset polymer or mixtures thereof, 0 to 55% by weight of additives and 0 to 55% by weight of filler or reinforcing materials, where the sum of the components is 100% by weight.

Finally, the invention also relates to a flame-retardant thermoplastic or thermoset polymer molding composition and to polymer moldings, films, filaments and fibers comprising 1 to 30% by weight of mixtures of at least one dialkylphosphinic acid of the formula (I) and at least one different dialkylphosphinic acid of the formula (II), 10 to 95% by weight of thermoplastic or thermoset polymer or mixtures thereof, 2 to 30% by weight of additives and 2 to 30% by weight of filler or reinforcing materials, where the sum of the components is 100% by weight.

Mixtures of at least one dialkylphosphinic acid of the formula (I) and at least one different dialkylphosphinic acid of the formula (II) are described, with the proviso that at least one of the $R^3$ and $R^4$ radicals is different than $R^1$ and $R^2$. This means that either $R^3$ or $R^4$ is different than $R^1$ and $R^2$ or else both are different, i.e. $R^3$ and $R^4$ are different than $R^1$ and $R^2$.

Preferably mixtures of at least one dialkylphosphinic acid of the formula (I) and at least one different dialkylphosphinic acid of the formula (II) are composed of dimethylphosphinic acid and methylethylphosphinic acid, dimethylphosphinic acid and methylpropylphosphinic acid, dimethylphosphinic acid and methylbutylphosphinic acid, dimethylphosphinic acid and methylpentylphosphinic acid, dimethylphosphinic acid and methylhexylphosphinic acid, dimethylphosphinic acid and ethylethylphosphinic acid, dimethylphosphinic acid and ethylpropylphosphinic acid, dimethylphosphinic acid and ethylbutylphosphinic acid, dimethylphosphinic acid and ethylpentylphosphinic acid, dimethylphosphinic acid and ethylhexylphosphinic acid, dimethylphosphinic acid and propylpropylphosphinic acid, dimethylphosphinic acid and propylbutylphosphinic acid, dimethylphosphinic acid and propylpentylphosphinic acid, dimethylphosphinic acid and propylhexylphosphinic acid, dimethylphosphinic acid and butylbutylphosphinic acid, dimethylphosphinic acid and butylpentylphosphinic acid, dimethylphosphinic acid and butylhexylphosphinic acid, dimethylphosphinic acid and pentylpentylphosphinic acid, dimethylphosphinic acid and pentylhexylphosphinic acid, dimethylphosphinic acid and hexylhexylphosphinic acid, diethylphosphinic acid and methylethylphosphinic acid, diethylphosphinic acid and methylpropylphosphinic acid, diethylphosphinic acid and methylbutylphosphinic acid, diethylphosphinic acid and methylpentylphosphinic acid, diethylphosphinic acid and methylhexylphosphinic acid, diethylphosphinic acid and ethylpropylphosphinic acid, diethylphosphinic acid and ethylbutylphosphinic acid, diethylphosphinic acid and ethylpentylphosphinic acid, diethylphosphinic acid and ethylhexylphosphinic acid, diethylphosphinic acid and propylpropylphosphinic acid, diethylphosphinic acid and propylbutylphosphinic acid, diethylphosphinic acid and propylpentylphosphinic acid, diethylphosphinic acid and propylhexylphosphinic acid, diethylphosphinic acid and butylbutylphosphinic acid, diethylphosphinic acid and butylpentylphosphinic acid, diethylphosphinic acid and butylhexylphosphinic acid, diethylphosphinic acid and pentylpentylphosphinic acid, diethylphosphinic acid and pentylhexylphosphinic acid, diethylphosphinic acid and hexylhexylphosphinic acid, dipropylphosphinic acid and methylethylphosphinic acid, dipropylphosphinic acid and methylpropylphosphinic acid, dipropylphosphinic acid and methylbutylphosphinic acid, dipropylphosphinic acid and methylpentylphosphinic acid, dipropylphosphinic acid and methylhexylphosphinic acid, dipropylphosphinic acid and ethylpropylphosphinic acid, dipropylphosphinic acid and ethylbutylphosphinic acid, dipropylphosphinic acid and ethylpentylphosphinic acid, dipropylphosphinic acid and ethylhexylphosphinic acid, dipropylphosphinic acid and propylbutylphosphinic acid, dipropylphosphinic acid and propylpentylphosphinic acid, dipropylphosphinic acid and propylhexylphosphinic acid, dipropylphosphinic acid and butylbutylphosphinic acid, dipropylphosphinic acid and butylpentylphosphinic acid, dipropylphosphinic acid and butylhexylphosphinic acid, dipropylphosphinic acid and pentylpentylphosphinic acid, dipropylphosphinic acid and pentylhexylphosphinic acid, dipropylphosphinic acid and hexylhexylphosphinic acid, dibutylphosphinic acid and methylethylphosphinic acid, dibutylphosphinic acid and methylpropylphosphinic acid, dibutylphosphinic acid and methylbutylphosphinic acid, dibutylphosphinic acid and methylpentylphosphinic acid, dibutylphosphinic acid and methylhexylphosphinic acid, dibutylphosphinic acid and ethylpropylphosphinic acid, dibutylphosphinic acid and ethylbutylphosphinic acid, dibutylphosphinic acid and ethylpentylphosphinic acid, dibutylphosphinic acid and ethylhexylphosphinic acid, dibutylphosphinic acid and propylbutylphosphinic acid, dibutylphosphinic acid and propylpentylphosphinic acid, dibutylphosphinic acid and propylhexylphosphinic acid, dibutylphosphinic acid and butylpentylphosphinic acid, dibutylphosphinic acid and butylhexylphosphinic acid, dibutylphosphinic acid and pentylpentylphosphinic acid, dibutylphosphinic acid and pentylhexylphosphinic acid, dibutylphosphinic acid and hexylhexylphosphinic acid, dipentylphosphinic acid and methylethylphosphinic acid, dipentylphosphinic acid and methylpropylphosphinic acid, dipentylphosphinic acid and methylbutylphosphinic acid, dipentylphosphinic acid and methylpentylphosphinic acid, dipentylphosphinic acid and methylhexylphosphinic acid, dipentylphosphinic acid and ethylpropylphosphinic acid, dipentylphosphinic acid and ethylbutylphosphinic acid, dipentylphosphinic acid and ethylpentylphosphinic acid, dipentylphosphinic acid and ethylhexylphosphinic acid, dipentylphosphinic acid and propylbutylphosphinic acid, dipentylphosphinic acid and propylpentylphosphinic acid, dipentylphosphinic acid and propylhexylphosphinic acid, dipentylphosphinic acid and butylpentylphosphinic acid, dipentylphosphinic acid and butylhexylphosphinic acid, dipentylphosphinic acid and pentylhexylphosphinic acid, dipentylphosphinic acid and hexylhexylphosphinic acid, dihexylphosphinic acid and methylethylphosphinic acid, dihexylphosphinic acid and methylpropylphosphinic acid, dihexylphosphinic acid and methylbutylphosphinic acid, dihexylphosphinic acid and methylpentylphosphinic acid, dihexylphosphinic acid and methylhexylphosphinic acid, dihexylphosphinic acid and ethylpropylphosphinic acid, dihexylphosphinic acid and ethylbutylphosphinic acid, dihexylphosphinic acid and ethylpentylphosphinic acid, dihexylphosphinic acid and ethylhexylphosphinic acid, dihexylphosphinic acid and propylbutylphosphinic acid, dihexylphosphinic acid and propylpentylphosphinic acid, dihexylphosphinic acid and propylhexylphosphinic acid, dihexylphosphinic acid and butylpentylphosphinic acid, dihexylphosphinic acid and butylhexylphosphinic acid, dihexylphosphinic acid and pentylhexylphosphinic acid, methylethylphosphinic acid and methylpropylphosphinic acid, methylethylphosphinic acid and methylbutylphosphinic acid, methylethylphosphinic acid and methylpentylphosphinic acid, methylethylphosphinic acid and methylhexylphosphinic acid, methylethylphosphinic acid and ethylpropylphosphinic acid, methylethylphosphinic acid and ethylbutylphosphinic acid, methylethylphosphinic acid and ethylpentylphosphinic acid, methylethylphosphinic acid and ethylhexylphosphinic acid, methylethylphosphinic acid and propylbutylphosphinic acid, methylethylphosphinic acid and propylpentylphosphinic acid, methylethylphosphinic acid and propylhexylphosphinic acid, methylethylphosphinic acid and butylpentylphosphinic acid, methylethylphosphinic acid and butylhexylphosphinic acid, methylethylphosphinic acid and pentylhexylphosphinic acid, methylpropylphosphinic acid and methylbutylphosphinic acid, methylpropylphosphinic acid and methylpentylphosphinic acid, methylpropylphosphinic acid and methylhexylphosphinic acid, methylpropylphosphinic acid and ethylpropylphosphinic acid, methylpropylphosphinic acid and ethylbutylphosphinic acid, methylpropylphosphinic acid and ethylpentylphosphinic acid, methylpropylphosphinic acid and ethylhexylphosphinic acid, methylpropylphosphinic acid and propylbutylphosphinic acid, methylpropylphosphinic acid and propylpentylphosphinic acid, methylpropylphosphinic acid and propylhexylphosphinic acid, methylpropylphosphinic acid and butylpentylphosphinic acid, methylpropylphosphinic acid and butylhexylphosphinic acid, methylpropylphosphinic acid and pentylhexylphosphinic acid, methylbutylphosphinic acid and methylpentylphosphinic acid, methylbutylphosphinic acid and methylhexylphosphinic acid, methylbutylphosphinic acid and ethylpropylphosphinic acid, methylbutylphosphinic acid and ethylbutylphosphinic acid, methylbutylphosphinic acid and ethylpentylphosphinic acid, methylbutylphosphinic acid and ethylhexylphosphinic acid, methylbutylphosphinic acid and propylbutylphosphinic acid, methylbutylphosphinic acid and propylpentylphosphinic acid, methylbutylphosphinic acid and propylhexylphosphinic acid, methylbutylphosphinic acid and butylpentylphosphinic acid, methylbutylphosphinic acid and butylhexylphosphinic acid, methylbutylphosphinic acid and pentylhexylphosphinic acid, methylpentylphosphinic acid and methylhexylphosphinic acid, methylpentylphosphinic acid and ethylpropylphosphinic acid, methylpentylphosphinic acid and ethylbutylphosphinic acid, methylpentylphosphinic acid and ethylpentylphosphinic acid, methylpentylphosphinic acid and ethylhexylphosphinic acid, methylpentylphosphinic acid and propylbutylphosphinic acid, methylpentylphosphinic acid and propylpentylphosphinic acid, methylpentylphosphinic acid and propylhexylphosphinic acid, methylpentylphosphinic acid and butylpentylphosphinic acid, methylpentylphosphinic acid and butylhexylphosphinic acid, methylpentylphosphinic acid and pentylhexylphosphinic acid, methylhexylphosphinic acid and ethylpropylphosphinic acid, methylhexylphosphinic acid and ethylbutylphosphinic acid, methylhexylphosphinic acid and ethylpentylphosphinic acid, methylhexylphosphinic acid and ethylhexylphosphinic acid, methylhexylphosphinic acid and propylbutylphosphinic acid, methylhexylphosphinic acid and propylpentylphosphinic acid, methylhexylphosphinic acid and propylhexylphosphinic acid, methylhexylphosphinic acid and butylpentylphosphinic acid, methylhexylphosphinic acid and butylhexylphosphinic acid, methylhexylphosphinic acid and pentylhexylphosphinic acid, ethylpropylphosphinic acid and ethylbutylphosphinic acid, ethylpropylphosphinic acid and ethylpentylphosphinic acid, ethylpropylphosphinic acid and ethylhexylphosphinic acid, ethylpropylphosphinic acid and propylbutylphosphinic acid, ethylpropylphosphinic acid and propylpentylphosphinic acid, ethylpropylphosphinic acid and propylhexylphosphinic acid, ethylpropylphosphinic acid and butylpentylphosphinic acid, ethylpropylphosphinic acid and butylhexylphosphinic acid, ethylpropylphosphinic acid and pentylhexylphosphinic acid, ethylbutylphosphinic acid and ethylpropylphosphinic acid, ethylbutylphosphinic acid and ethylpentylphosphinic acid, ethylbutylphosphinic acid and ethylhexylphosphinic acid, ethylbutylphosphinic acid and propylbutylphosphinic acid, ethylbutylphosphinic acid and propylpentylphosphinic acid, ethylbutylphosphinic acid and propylhexylphosphinic acid, ethylbutylphosphinic acid and butylpropylphosphinic acid, ethylbutylphosphinic acid and butylpentylphosphinic acid, ethylbutylphosphinic acid and butylhexylphosphinic acid, ethylbutylphosphinic acid and pentylethylphosphinic acid, ethylbutylphosphinic acid and pentylpropylphosphinic acid, ethylbutylphosphinic acid and pentylbutylphosphinic acid, ethylbutylphosphinic acid and pentylhexylphosphinic acid, ethylpentylphosphinic acid and ethylpropylphosphinic acid, ethylpentylphosphinic acid and ethylbutylphosphinic acid, ethylpentylphosphinic acid and ethylhexylphosphinic acid, ethylpentylphosphinic acid and propylbutylphosphinic acid, ethylpentylphosphinic acid and propylpentylphosphinic acid, ethylpentylphosphinic acid and propylhexylphosphinic acid, ethylpentylphosphinic acid and butylpropylphosphinic acid, ethylpentylphosphinic acid and butylpentylphosphinic acid, ethylpentylphosphinic acid and butylhexylphosphinic acid, ethylpentylphosphinic acid and pentylpropylphosphinic acid, ethylpentylphosphinic acid and pentylbutylphosphinic acid, ethylpentylphosphinic acid and pentylhexylphosphinic acid, ethylhexylphosphinic acid and ethylpropylphosphinic acid, ethylhexylphosphinic acid and ethylbutylphosphinic acid, ethylhexylphosphinic acid and ethylhexylphosphinic acid, ethylhexylphosphinic acid and propylbutylphosphinic acid, ethylhexylphosphinic acid and propylpentylphosphinic acid, ethylhexylphosphinic acid and propylhexylphosphinic acid, ethylhexylphosphinic acid and butylpropylphosphinic acid, ethylhexylphosphinic acid and butylpentylphosphinic acid, ethylhexylphosphinic acid and butylhexylphosphinic acid, ethylhexylphosphinic acid and pentylpropylphosphinic acid, ethylhexylphosphinic acid and pentylbutylphosphinic acid, ethylhexylphosphinic acid and pentylhexylphosphinic acid, propylbutylphosphinic acid and propylpentylphosphinic acid, propylbutylphosphinic acid and propylhexylphosphinic acid, propylbutylphosphinic acid and butylpentylphosphinic acid, propylbutylphosphinic acid and butylhexylphosphinic acid, propylbutylphosphinic acid and pentylpropylphosphinic acid, propylbutylphosphinic acid and pentylbutylphosphinic acid, propylbutylphosphinic acid and pentylhexylphosphinic acid, propylbutylphosphinic acid and hexylbutylphosphinic acid, propylbutylphosphinic acid and hexylpropylphosphinic acid, propylpentylphosphinic acid and propylhexylphosphinic acid, propylpentylphosphinic acid and butylpentylphosphinic acid, propylpentylphosphinic acid and butylhexylphosphinic acid, propylpentylphosphinic acid and pentylbutylphosphinic acid, propylpentylphosphinic acid and pentylhexylphosphinic acid, propylhexylphosphinic acid and butylhexylphosphinic acid, propylhexylphosphinic acid and pentylbutylphosphinic acid, propylhexylphosphinic acid and pentylhexylphosphinic acid, butylpentylphosphinic acid and butylhexylphosphinic acid, butylpentylphosphinic acid and pentylhexylphosphinic acid, butylpentylphosphinic acid and hexylbutylphosphinic acid, butylpentylphosphinic acid and hexylpentylphosphinic acid, butylhexylphosphinic acid and pentylhexylphosphinic acid.

This list also includes all variations, for example n-, iso-, tert- etc., i.e., for instance, tert-butylisopentylphosphinic acid and isohexyl-n-pentylphosphinic acid and all other conceivable mixtures.

In addition, multicomponent mixtures may also occur, for example those of dimethylphosphinic acid and methylethylphosphinic acid and methylpropylphosphinic acid, diethylphosphinic acid and methylethylphosphinic acid and dipropylphosphinic acid etc.; accordingly, four-component mixtures and mixtures with a higher number of the aforementioned diphosphinic acids are also possible.

Particular preference is given to mixtures of dimethylphosphinic acid and butylethylphosphinic acid, diethylphosphinic acid and butylethylphosphinic acid, dipropylphosphinic acid and butylethylphosphinic acid, dibutylphosphinic acid and butylethylphosphinic acid, dimethylphosphinic acid and hexylethylphosphinic acid, diethylphosphinic acid and hexylethylphosphinic acid.

The mixture preferably comprises 0.1 to 99.9% by weight of diphosphinic acid of the formula (I) and 99.9 to 0.1% by weight of butylalkylphosphinic acid of the formula (II).

The mixture more preferably comprises 99.9 to 50% by weight of diphosphinic acid of the formula (I) and 0.1 to 50% by weight of butylalkylphosphinic acid of the formula (II).

The mixture more preferably also comprises 80 to 99.5% by weight of diphosphinic acid of the formula (I) and 0.5 to 20% by weight of butylalkylphosphinic acid of the formula (II).

The mixture especially preferably comprises 95 to 99.9% by weight of diphosphinic acid of the formula (I) and 0.1 to 5% by weight of butylalkylphosphinic acid of the formula (II).

The preferred diphosphinic acid of the formula (I) is diethylphosphinic acid, and the preferred butylalkylphosphinic acid of the formula (II) is butylethylphosphinic acid.

The invention encompasses especially mixtures consisting of 98 to 99.9% by weight of diethylphosphinic acid and 2 to 0.1% by weight of butylethylphosphinic acid.

As stated above, the mixture preferably further comprises at least one synergist. The synergist is preferably at least one expansion-neutral substance, which means that its dimensions do not change under thermal or similar stress. Such changes can be determined by means of the coefficient of thermal expansion. This describes the changes in the dimensions of a substance in the event of temperature changes.

The mixtures preferably comprise 65 to 1% by weight of the mixture of at least one dialkylphosphinic acid of the formula (I) and at least one dialkylphosphinic acid of the formula (II) and 1 to 35% by weight of synergist.

The mixtures preferably also comprise 80 to 95% by weight of the mixture of at least one dialkylphosphinic acid of the formula (I) and at least one dialkylphosphinic acid of the formula (II) and 5 to 20% by weight of synergist.

In the process according to the invention, the solvent used is preferably acetic acid or water and the reaction temperature is preferably 80 to 120° C.

Preference is given to processing the inventive mixture of at least one dialkylphosphinic acid of the formula (I) and at least one different dialkylphosphinic acid of the formula (II) by mixing it into a polymer system.

The mixing is effected by kneading, dispersing and/or extruding.

Preference is given to using the inventive mixture of at least one dialkylphosphinic acid of the formula (I) and at least one different dialkylphosphinic acid of the formula (II) by additive incorporation into a polymer system.

Particular preference is given to using the mixtures of at least one dialkylphosphinic acid of the formula (I) and at least one different dialkylphosphinic acid of the formula (II) by reactive incorporation into a polymer system. Reactive incorporation is characterized by a resulting permanent bond to the polymer extrudates of the polymer system, as a result of which the inventive mixture of at least one dialkylphosphinic acid of the formula (I) and at least one different dialkylphosphinic acid of the formula (II) cannot be leached out.

The inventive mixtures can be used with further flame retardants and further synergists. The further flame retardants include, for example, phosphorus compounds such as phosphinates, phosphonates, phosphates, phosphonic acids, phosphinic acids, phosphoric acids, phosphines, phosphine oxides, phosphorus oxides and others.

Suitable polymer additives for flame-retardant polymer molding compositions and polymer moldings are UV absorbers, light stabilizers, lubricants, colorants, antistats, nucleating agents, fillers, synergists, reinforcers and others.

The polymer systems preferably originate from the group of the thermoplastic polymers such as polyamide, polyester or polystyrene and/or thermoset polymers.

The thermoset polymers are more preferably epoxy resins.

The thermoset polymers are more preferably epoxy resins which have been cured with phenols and/or dicyandiamide [more generally: phenol derivatives (resols); alcohols and amines], especially phenol derivatives and dicyandiamide.

The thermoset polymers are more preferably epoxy resins which have been cured with phenols and/or dicyandiamide and/or a catalyst.

The catalysts are preferably imidazole compounds.

The epoxy resins are preferably polyepoxide compounds.

The epoxy resins are preferably resins based on novolac and/or bisphenol A.

The polymers are preferably polymers of mono- and diolefins, for example polypropylene, polyisobutylene, polybutene-1, poly-4-methylpentene-1, polyisoprene or polybutadiene, and addition polymers of cycloolefins, for example of cyclopentene or norbornene; and also polyethylene (which may optionally be crosslinked), e.g. high-density polyethylene (HDPE), high-density high-molar mass polyethylene (HDPE-HMW), high-density ultrahigh-molar mass polyethylene (HDPE-UHMW), medium-density polyethylene (MDPE), low-density polyethylene (LDPE), linear low-density polyethylene (LLDPE), branched low-density polyethylene (BLDPE), and mixtures thereof.

The polymers are preferably copolymers of mono- and diolefins with one another or with other vinyl monomers, for example ethylene-propylene copolymers, linear low-density polyethylene (LLDPE) and mixtures thereof with low-density polyethylene (LDPE), propylene-butene-1 copolymers, propylene-isobutylene copolymers, ethylene-butene-1 copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and copolymers thereof with carbon monoxide, or ethylene-acrylic acid copolymers and salts thereof (ionomers), and also terpolymers of ethylene with propylene and a diene such as hexadiene, dicyclopentadiene or ethylidenenorbornene; and also mixtures of such copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene/carbon monoxide copolymers and mixtures thereof with other polymers, for example polyamides.

The polymers are preferably hydrocarbon resins (e.g. $C_5$-$C_9$), including hydrogenated modifications thereof (e.g. tackifier resins) and mixtures of polyalkylenes and starch.

The polymers are preferably polystyrene (Polystyrol® 143E (BASF), poly(p-methylstyrene), poly(alpha-methylstyrene).

The polymers are preferably copolymers of styrene or alpha-methylstyrene with dienes or acrylic derivatives, for example styrene-butadiene, styrene-acrylonitrile, styrene-alkyl methacrylate, styrene-butadiene-alkyl acrylate and methacrylate, styrene-maleic anhydride, styrene-acrylonitrile-methyl acrylate; more impact-resistant mixtures of styrene copolymers and another polymer, for example a polyacrylate, a diene polymer or an ethylene-propylene-diene terpolymer; and block copolymers of styrene, for example styrene-butadiene-styrene, styrene-isoprene-styrene, styrene-ethylene/butylene-styrene or styrene-ethylene/propylene-styrene.

The polymers are preferably graft copolymers of styrene or alpha-methylstyrene, for example styrene onto polybutadiene, styrene onto polybutadiene-styrene or polybutadiene-acrylonitrile copolymers, styrene and acrylonitrile (or methacrylonitrile) onto polybutadiene; styrene, acrylonitrile and methyl methacrylate onto polybutadiene; styrene and maleic anhydride onto polybutadiene; styrene, acrylonitrile and maleic anhydride or maleimide onto polybutadiene; styrene and maleimide onto polybutadiene, styrene and alkyl acrylates or alkyl methacrylates onto polybutadiene, styrene and acrylonitrile onto ethylene-propylene-diene terpolymers, styrene and acrylonitrile onto polyalkyl acrylates or polyalkyl methacrylates, styrene and acrylonitrile onto acrylate-butadiene copolymers, and mixtures thereof, as known, for example, as ABS, MBS, ASA or AES polymers.

The styrene polymers are preferably comparatively coarse-pore foam such as EPS (expanded polystyrene), e.g. Styropor (BASF) and/or foam with relatively fine pores such as XPS (extruded rigid polystyrene foam), e.g. Styrodur® (BASF). Preference is given to polystyrene foams, for example Austrotherm® XPS, Styrofoam® (Dow Chemical), Floormate®, Jackodur®, Lustron®, Roofmate®, Sagex® and Telgopor®.

The polymers are preferably halogenated polymers, for example polychloroprene, chlorine rubber, chlorinated and brominated copolymer of isobutylene-isoprene (halobutyl rubber), chlorinated or chlorosulfonated polyethylene, copolymers of ethylene and chlorinated ethylene, epichlorohydrin homo- and copolymers, especially polymers of halogenated vinyl compounds, for example polyvinyl chloride, polyvinylidene chloride, polyvinyl fluoride, polyvinylidene fluoride; and copolymers thereof, such as vinyl chloride-vinylidene chloride, vinyl chloride-vinyl acetate or vinylidene chloride-vinyl acetate.

The polymers are preferably polymers which derive from alpha, beta-unsaturated acids and derivatives thereof, such as polyacrylates and polymethacrylates, polymethyl methacrylates, polyacrylamides and polyacrylonitriles impact-modified with butyl acrylate, and copolymers of the monomers mentioned with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

The polymers are preferably polymers which derive from unsaturated alcohols and amines or the acyl derivatives or acetals thereof, such as polyvinyl alcohol, polyvinyl acetate, stearate, benzoate or maleate, polyvinyl butyral, polyallyl phthalate, polyallylmelamine; and copolymers thereof with olefins.

The polymers are preferably homo- and copolymers of cyclic ethers, such as polyalkylene glycols, polyethylene oxide, polypropylene oxide or copolymers thereof with bisglycidyl ethers.

The polymers are preferably polyacetals such as polyoxymethylene, and those polyoxymethylenes which contain comonomers, for example ethylene oxide; polyacetals which have been modified with thermoplastic polyurethanes, acrylates or MBS.

The polymers are preferably polyphenylene oxides and sulfides and mixtures thereof with styrene polymers or polyamides.

The polymers are preferably polyurethanes which derive from polyethers, polyesters and polybutadienes having both terminal hydroxyl groups and aliphatic or aromatic polyisocyanates, and the precursors thereof.

The polymers are preferably polyamides and copolyamides which derive from diamines and dicarboxylic acids and/or from aminocarboxylic acids or the corresponding lactams, such as nylon 2/12, nylon 4 (poly-4-aminobutyric acid, Nylon® 4, from DuPont), nylon 4/6 (poly(tetramethyleneadipamide), Nylon® 4/6, from DuPont), nylon 6 (polycaprolactam, poly-6-aminohexanoic acid, Nylon® 6, from DuPont, Akulon K122, from DSM; Zytel® 7301, from DuPont; Durethan® B 29, from Bayer), nylon 6/6 (poly(N, N'-hexamethyleneadipamide), Nylon® 6/6, from DuPont, Zytel® 101, from DuPont; Durethan A30, Durethan® AKV, Durethan® AM, from Bayer; Ultramid® A3, from BASF), nylon 6/9 (poly(hexamethylenenonanamide), Nylon® 6/9, from DuPont), nylon 6/10 (poly(hexamethylenesebacamide), Nylon® 6/10, from DuPont), nylon 6/12 (poly(hexamethylenedodecanediamide), Nylon® 6/12, from DuPont), nylon 6/66 (poly(hexamethyleneadipamide-co-caprolactam), Nylon® 6/66, from DuPont), nylon 7 (poly-7-aminoheptanoic acid, Nylon® 7, from DuPont), nylon 7,7 (polyheptamethylenepimelamide, Nylon® 7,7, from DuPont), nylon 8 (poly-8-aminooctanoic acid, Nylon® 8, from DuPont), nylon 8,8 (polyoctamethylenesuberamide, Nylon® 8,8, from DuPont), nylon 9 (poly-9-aminononanoic acid, Nylon® 9, from DuPont), nylon 9,9 (polynonamethyleneazelamide, Nylon® 9,9, from DuPont), nylon 10 (poly-10-aminodecanoic acid, Nylon® 10, from DuPont), nylon 10,9 (poly(decamethyleneazelamide), Nylon® 10,9, from DuPont), nylon 10,10 (polydecamethylenesebacamide, Nylon® 10,10, from DuPont), nylon 11 (poly-11-aminoundecanoic acid, Nylon® 11, from DuPont), nylon 12 (polylauryllactam, Nylon® 12, from DuPont, Grillamid® L20, from Ems Chemie), aromatic polyamides proceeding from m-xylene, diamine and adipic acid; polyamides prepared from hexamethylenediamine and iso- and/or terephthalic acid (polyhexamethyleneisophthalamide, polyhexamethyleneterephthalamide) and optionally an elastomer as a modifier, e.g. poly-2,4,4-trimethylhexamethyleneterephthalamide or poly-m-phenyleneisophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM (ethylene-propylene-diene rubber) or ABS (acrylonitrile-butadiene-styrene); and polyamides condensed during processing ("RIM polyamide systems").

The polymers are preferably polyureas, polyimides, polyamidimides, polyetherimides, polyesterimides, polyhydantoins and polybenzimidazoles.

The polymers are preferably polyesters which derive from dicarboxylic acids and dialcohols and/or from hydroxycarboxylic acids or the corresponding lactones, such as polyethylene terephthalate, polybutylene terephthalate (Celanex® 2500, Celanex®2002, from Celanese; Ultradur®, from BASF), poly-1,4-dimethylolcyclohexane terephthalate, polyhydroxybenzoates, and block polyether esters which derive from polyethers with hydroxyl end groups; and also polyesters modified with polycarbonates or MBS.

The polymers are preferably polycarbonates and polyester carbonates.

The polymers are preferably polysulfones, polyether sulfones and polyether ketones.

Preferably, the polymers are crosslinked polymers which derive from aldehydes on the one hand, and phenols, urea or melamine on the other hand, such as phenol-formaldehyde, urea-formaldehyde and melamine-formaldehyde resins.

The polymers are preferably drying and nondrying alkyd resins.

The polymers are preferably unsaturated polyester resins which derive from copolyesters of saturated and unsaturated dicarboxylic acids with polyhydric alcohols, and vinyl compounds as crosslinking agents, and also the halogenated, flame-retardant modifications thereof.

The polymers are preferably crosslinkable acrylic resins which derive from substituted acrylic esters, for example from epoxy acrylates, urethane acrylates or polyester acrylates.

Preferably, the polymers are alkyd resins, polyester resins and acrylate resins which have been crosslinked with melamine resins, urea resins, isocyanates, isocyanurates, polyisocyanates or epoxy resins.

The polymers are preferably crosslinked epoxy resins which derive from aliphatic, cycloaliphatic, heterocyclic or aromatic glycidyl compounds, for example products of bisphenol A diglycidyl ethers, bisphenol F diglycidyl ethers, which are crosslinked by means of customary hardeners, for example anhydrides or amines, with or without accelerators.

The polymers are preferably mixtures (polyblends) of the abovementioned polymers, for example PP/EPDM (polypropylene/ethylene-propylene-diene rubber), polyamide/EPDM or ABS (polyamide/ethylene-propylene-diene rubber or acrylonitrile-butadiene-styrene), PVC/EVA (polyvinyl chloride/ethylene-vinyl acetate), PVC/ABS (polyvinyl chloride/acrylonitrile-butadiene-styrene), PVC/MBS (polyvinyl chloride/methacrylate-butadiene-styrene), PC/ABS (polycarbonate/acrylonitrile-butadiene-styrene), PBTP/ABS (polybutylene terephthalate/acrylonitrile-butadiene-styrene), PC/ASA (polycarbonate/acrylic ester-styrene-acrylonitrile), PC/PBT (polycarbonate/polybutylene terephthalate), PVC/CPE (polyvinyl chloride/chlorinated polyethylene), PVC/acrylate (polyvinyl chloride/acrylate), POM/thermoplastic PUR (polyoxymethylene/thermoplastic polyurethane), PC/thermoplastic PUR (polycarbonate/thermoplastic polyurethane), POM/acrylate (polyoxymethylene/acrylate), POM/MBS (polyoxymethylene/methacrylate-butadiene-styrene), PPO/HIPS (polyphenylene oxide/high-impact polystyrene), PPO/PA 6,6 (polyphenylene oxide/nylon 6,6) and copolymers, PA/HDPE (polyamide/high-density polyethylene), PA/PP (polyamide/polyethylene), PA/PPO (polyamide/polyphenylene oxide), PBT/PC/ABS (polybutylene terephthalate/polycarbonate/acrylonitrile-butadiene-styrene) and/or PBT/PET/PC (polybutylene terephthalate/polyethylene terephthalate/polycarbonate).

The molding composition produced is preferably of rectangular shape with a regular or irregular base, or of cubic shape, cuboidal shape, cushion shape or prism shape.

The invention is illustrated by the examples which follow.

Production, Processing and Testing of Flame-Retardant Polymer Molding Compositions and Flame-Retardant Polymer Moldings The flame-retardant components are mixed with the polymer pellets and any additives and incorporated in a twin-screw extruder (model: Leistritz LSM® 30/34) at temperatures of 230 to 260° C. (PBT-GR) or of 260 to 280° C. (PA 66-GR). The homogenized polymer strand was drawn off, cooled in a water bath and then pelletized.

After sufficient drying, the molding compositions were processed on an injection molding machine (model: Aarburg Allrounder) at melt temperatures of 240 to 270° C. (PBT-GR) or of 260 to 290° C. (PA 66-GR) to give test specimens. The test specimens are tested for flame retardancy and classified using the UL 94 test (Underwriter Laboratories).

Test specimens of each mixture were used to determine the UL 94 fire class (Underwriter Laboratories) on specimens of thickness 1.5 mm. The UL 94 fire classifications are as follows:

V-0: afterflame time never longer than 10 sec., total of afterflame times for 10 flame applications not more than 50 sec., no flaming drops, no complete consumption of the specimen, afterglow time for specimens never longer than 30 sec. after end of flame application.
V-1: afterflame time never longer than 30 sec. after end of flame application, total of afterflame times for 10 flame applications not more than 250 sec., afterglow time for specimens never longer than 60 sec. after end of flame application, other criteria as for V-0.
V-2: cotton indicator ignited by flaming drops, other criteria as for V-1.
Not classifiable (ncl): does not fulfill fire class V-2.

For some samples examined, the LOI was also measured. The LOI (Limiting Oxygen Index) is determined to ISO 4589 and corresponds to the lowest oxygen concentration in percent by volume which just still supports the combustion of the polymer in a mixture of oxygen and nitrogen. The higher the LOI the greater the nonflammability of the material tested.

LOI 23 flammable
LOI 24-28 limited flammability
LOI 29-35 flame-retardant
LOI>36 particularly flame-retardant Chemicals and Abbreviations Used
Phenol novolac: Bakelite® PF 0790, from Hexion
Initiator: Vazo 67, from DuPont

EXAMPLE 1

According to EP-A-1544205, example 8, a diethylphosphinic acid metal salt solution is obtained from sodium hypophosphite by means of initiator and ethylene.

Subsequent treatment of the product solution with dilute sulfuric acid, concentration, filtration and distillation at 184° C. (1 mbar) give a yield of 94% of a mixture of diethylphosphinic acid (99.9% by weight) and butylethylphosphinic acid (0.01% by weight).

EXAMPLE 2

According to EP-A-1544205, example 8, a diethylphosphinic acid metal salt solution is obtained from sodium hypophosphite by means of initiator and ethylene. Treatment of the product solution with dilute sulfuric acid, concentration, filtration and distillation at 180-190° C. (1 mbar) give a yield of 92% of a mixture of diethylphosphinic acid (98% by weight) and butylethylphosphinic acid (2% by weight).

EXAMPLE 3

Diethylphosphinic acid is obtained analogously to EP-A-1544205, example 8, from sodium hypophosphite by means of initiator and ethylene, and is purified by means of subsequent distillation.

Butylethylphosphinic acid is synthesized by reaction of ethylphosphinic acid with butene analogously to WO-A-2009/010188. A mixture of diethylphosphinic acid and butylethylphosphinic acid in a weight ratio of 90:10 is obtained by mixing the two pure components.

EXAMPLE 4

In a manner corresponding to example 3, a mixture of diethylphosphinic acid and butylethylphosphinic acid in a weight ratio of 60:40 is obtained by mixing the two pure components.

EXAMPLE 5

In a manner corresponding to example 3, a mixture of diethylphosphinic acid and butylethylphosphinic acid in a weight ratio of 50:50 is obtained by mixing the two pure components.

General method for producing polymer moldings:
a) Preparation of phosphorus-modified epoxy resin
  A 2 l five-neck flask apparatus is initially charged with 1000 g of the epoxy resin (e.g. Beckopox EP 140). It is heated to 110° C. for one hour and volatile components are removed under reduced pressure. Thereafter, the reaction mixture is inertized with nitrogen and the temperature in the flask is increased to 170° C. 118 g of the mixture of the phosphorus compounds (selected from examples 1 to 5) are added in each case, while stirring under flowing nitrogen, and an exothermic reaction is observed. The resulting resin is yellow in color and free-flowing.

b) Production of epoxy resin specimens 100 parts of the phosphorus-modified epoxy resin are mixed with one corresponding OH equivalent of phenol novolac (hydroxide equivalents 105 g/mol, melting point 85-95° C.) and heated to 150° C. The mixture is stirred until a homogeneous mixture has formed and is allowed to cool to 130° C. Then 0.03 part 2-phenylimidazole is added and the mixture is stirred once again for 5-10 min. Thereafter, the mixture is poured warm into a dish and cured at 140° C. for 2 h and at 200° C. for 2 h.

c) Production of epoxy resin laminate 100 parts phosphorus-modified epoxy resin as per b) are added to 63 parts acetone and 27 parts Dowanol® PM, and the appropriate amount of phenol resin is added. The mixture is left to stir for 30 min. and 2-phenylimidazole is added. Thereafter, the mixture is filtered through a 400 μm sieve in order to remove excess resin particles. Then a woven glass fabric (7628 type, 203 g/m$^2$) is immersed into the solution until complete wetting of the fabric has taken place. The wetted fabric is pulled out of the mixture and excess resin is removed. Thereafter, the wetted fabric is initially cured in stages in a drying cabinet for a brief period at temperatures up to 165° C. and then fully cured in a heated press. The resin content of the cured laminates is 30-50%.

The thermal expansion of the molding produced, a laminate, is determined to ASTM E831-06.

EXAMPLE 6

According to the general method for producing a polymer molding, 100% of a bisphenol A resin is used to produce a laminate.

EXAMPLE 7

Diethylphosphinic acid is obtained analogously to patent EP-A-1544205, example 8, from sodium hypophosphite by means of initiator and ethylene, and is purified by means of subsequent distillation.

According to the general method for producing a polymer molding, a composition composed to 90% by weight of bisphenol A resin with hardener and catalyst and 10% by weight of diethylphosphinic acid is used to produce a molding.

EXAMPLE 8

Butylethylphosphinic acid is synthesized by reaction of ethylphosphinic acid with butene analogously to WO-A-2009/010188.

According to the general method for producing a polymer molding, a composition composed to 90% by weight of bisphenol A resin with hardener and catalyst and 10% by weight of butylethylphosphinic acid is used to produce a molding.

EXAMPLE 9

According to the general method for producing a polymer molding, a composition composed to 90% by weight of bisphenol A resin with hardener and catalyst and 10% by weight of the inventive mixture according to example 1 is used to produce a molding.

EXAMPLE 10

According to the general method for producing a polymer molding, a composition composed to 90% by weight of bisphenol A resin with hardener and catalyst and 10% by weight of the inventive mixture according to example 2 is used to produce a molding.

EXAMPLE 11

According to the general method for producing a polymer molding, a composition composed to 90% by weight of bisphenol A resin with hardener and catalyst and 10% by weight of the inventive mixture according to example 3 is used to produce a molding.

EXAMPLE 12

According to the general method for producing a polymer molding, a composition composed to 90% by weight of bisphenol A resin with hardener and catalyst and 10% by weight of the inventive mixture according to example 4 is used to produce a molding.

EXAMPLE 13

According to the general method for producing a polymer molding, a composition composed to 90% by weight of bisphenol A resin with hardener and catalyst and 10% by weight of the inventive mixture according to example 5 is used to produce a molding.

The results are reproduced in the following table:

| Example | Composition of polymer system/mixture [% by wt.] % by wt.] | Mixture of dialkylphosphinic acid of the formula (I)/dialkylphosphinic acid of the formula (II) [% by wt/% by wt] | Coefficient of thermal expansion 0°-100° [ppm/° C.] | | |
|---|---|---|---|---|---|
| | | | Z | X | Y |
| 6 | 100:0 | | 69 | 20 | 7 |
| 7 | 90:10 | 100:0 | 70 | 21 | 8 |
| 8 | 90:10 | 0:100 | 71 | 20 | 7 |
| 9 | 90:10 | 99.9:0.1 | 65 | 18 | 5 |
| 10 | 90:10 | 98:2 | 63 | 17 | 5 |
| 11 | 90:10 | 90:10 | 60 | 16 | 5 |
| 12 | 90:10 | 60:40 | 58 | 14 | 4 |
| 13 | 90:10 | 50:50 | 56 | 13 | 4 |

Compared to the pure laminate (example 6), there is a decrease in the values for the coefficient of thermal expansion of the laminate comprising the inventive mixture of diethylphosphinic acid and butylethylphosphinic acid; thermal expansion is thus very low. An increase in the butylethylphosphinic acid content brings about a further improvement. The inventive products lead to lower expansion of the moldings produced and thus meet the demands on dimensional stability.

The invention claimed is:

1. A flame-retardant thermoset composition or, film, comprising 0.5 to 45% by weight of a mixture of at least one dialkylphosphinic acid of the formula (I)

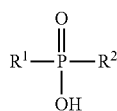

(I)

wherein
R¹, R² are the same or different and are $C_1$-$C_{18}$-alkyl, $C_2$-$C_{18}$-alkenyl, $C_6$-$C_{18}$-aryl or $C_7$-$C_{18}$-alkylaryl,
with at least one different dialkylphosphinic acid of the formula (II)

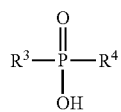

(II)

wherein
R³, R⁴ are the same or different and are $C_1$-$C_{18}$-alkyl, $C_2$-$C_{18}$-alkenyl, $C_6$-$C_{18}$-aryl or $C_7$-$C_{18}$-alkylaryl,
with the proviso that at least one of the R³ and R⁴ radicals is different than R¹ and R², 0.5 to 99.5% by weight of thermoset polymer, 0 to 55% by weight of additives and 0 to 55% by weight of filler or a reinforcing material, where the sum of the components is 100% by weight.

2. A flame-retardant thermoset composition or film, comprising 1 to 30% by weight of a mixture of at least one dialkylphosphinic acid of the formula (I)

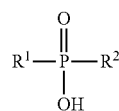

(I)

wherein
R¹, R² are the same or different and are $C_1$-$C_{18}$-alkyl, $C_2$-$C_{18}$-alkenyl, $C_6$-$C_{18}$-aryl or $C_7$-$C_{18}$-alkylaryl,
with at least one different dialkylphosphinic acid of the formula (II)

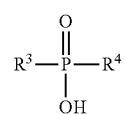

(II)

wherein
R³, R⁴ are the same or different and are $C_1$-$C_{18}$-alkyl, $C_2$-$C_{18}$-alkenyl, $C_6$-$C_{18}$-aryl or $C_7$-$C_{18}$-alkylaryl,
with the proviso that at least one of the R³ and R⁴ radicals is different than R¹ and R², 10 to 95% by weight of thermoset polymer, 2 to 30% by weight of additives and 2 to 30% by weight of filler or a reinforcing material, where the sum of the components is 100% by weight.

* * * * *